United States Patent [19]

Laud et al.

[11] 3,933,028
[45] Jan. 20, 1976

[54] AIR/FUEL RATIO SENSOR FOR AIR/FUEL RATIOS IN EXCESS OF STOICHIOMETRY

[75] Inventors: Kamlakar R. Laud, Ann Arbor; Eleftherios M. Logothetis, Birmingham; Kwansuh Park, Ann Arbor, all of Mich.

[73] Assignee: Ford Motor Company, Dearborn, Mich.

[22] Filed: Apr. 23, 1974

[21] Appl. No.: 463,345

[52] U.S. Cl............................ 73/23; 73/27 R; 338/34
[51] Int. Cl.²..................... G01N 7/02; G01N 31/00
[58] Field of Search .......... 73/23, 27 R; 338/34, 35; 324/65 P, 71 SN; 23/254 E

[56] References Cited
UNITED STATES PATENTS

| | | | |
|---|---|---|---|
| 3,539,471 | 11/1970 | Sproul | 338/35 X |
| 3,558,280 | 1/1971 | Panson et al. | 73/27 R X |
| 3,611,243 | 10/1971 | Hardtl | 338/34 |
| 3,623,364 | 11/1971 | Withrow | 73/204 |
| 3,695,848 | 10/1972 | Taguchi | 73/27 R X |
| 3,738,341 | 6/1973 | Loos | 73/23 X |

Primary Examiner—Charles A. Ruehl
Attorney, Agent, or Firm—Robert A. Benziger; Keith L. Zerschling

[57] ABSTRACT

The present invention provides a sensor which is operative to sense the partial pressure of oxygen in the exhaust gases of combustion processes having air/fuel combustion mixture ratios in excess of the stoichiometric ratio. The sensor according to the present invention relies upon the direct and generally linear change in the logarithm of the resistance of cobalt monoxide ceramic material as a function of the partial pressure of oxygen in the environment of the sensor element at elevated temperatures for partial pressures of oxygen which coincide with the partial pressures of oxygen in the exhaust gases of fuel-lean combustion mixtures. The present invention provides a generally cylindrical cobalt monoxide ceramic sensor element, supported within a housing formed of a compatible ceramic material such as alumina, and arranged so that the change in the electrical resistance between the ends of the cylinder of the sensing element may be measured. When the sensor is situated within the exhaust system of an internal combustion engine, the change in electrical resistance is a measure of the partial pressure of oxygen within the exhaust system and is also indicative of the air/fuel ratio of the combustion mixture which has produced the exhaust gases of the environment of the sensor. Such indication is usable to maintain the combustion mixture at a desired air/fuel ratio.

10 Claims, 5 Drawing Figures

AIR/FUEL RATIO SENSOR FOR AIR/FUEL RATIOS IN EXCESS OF STOICHIOMETRY

BACKGROUND OF THE INVENTION

1. Field of the Invention

The present invention is directed to the field of internal combustion engine analyzers. More particularly, the present invention is directed to that portion of the above-noted field which is concerned with the analysis of the air/fuel ratio of the combustion mixture provided to the engine. More particularly still, the present invention is directed to that portion of the above-noted field in which analysis of the chemistry of the exhaust gases produced by the engine results in a determination of the air/fuel ratio of the combustion mixture being provided to the engine. With greater particularity still, the present invention is directed to that portion of the above-noted field which is concerned with the provision of a sensor for accurately sensing the air/fuel ratio of a combustion mixture by changing an electrical characteristic in response to changes in the partial pressure of oxygen present in the exhaust gases resulting from the combustion process where the air/fuel ratio for the combustion mixture is to be maintained at a value in excess of the stoichiometric value.

2. Description of the Prior Art

The need for analyzing the operation of an internal combustion engine to improve or maintain the efficient operation thereof is well recognized. It has been suggested, at least as early as 1937, that the air-to-fuel ratio of a combustible mixture provided to an internal combustion engine may be determined by analyzing the composition of the exhaust gases produced from combustion of the mixture. An example of such a system appears in U.S. Pat. No. 2,077,538 — "Exhaust Gas Analyzer For Automotive Vehicles" issued in the name of L. S. Wait. According to the system disclosed in the Wait patent, a variable resistance element is situated in the exhaust stream of an internal combustion engine and arranged within an electrical bridge network, such as for example a Wheatstone bridge, so that the heat dissipative qualities of the variable resistance element will respond to changes in the chemistry of the exhaust gases to provide an indication of the air/fuel ratio of the combustion mixture being provided to the engine.

More recently, the efforts to reduce the pollution of our atmosphere have prompted implementation of stringent controls upon an automotive engine exhaust emissions. In efforts to reduce the amount of pollutants injected into our atmosphere by mobile internal combustion engines, it has become apparent that accurate and self-adjusting control of the air/fuel ratio of the combustion mixture provided to such engines is desirable. For example, copending commonly assigned U.S. Pat. No 3,868,846, issued on Mar. 4, 1975 in the names of T. Kushida et al. and titled "Circuit For Converting A Temperature Dependent Input Signal To A Temperature Independent Output Signal" discloses one system wherein a titania exhaust gas sensor is responsive to changes in the exhaust gas chemistry, caused by excursions of the air/fuel ratio of the combustion mixture being provided to the engine from a selected value at, or richer, in fuel than, the stoichiometric value, to automatically and reliably control a controller means to maintain the air/fuel ratio of the combustible mixture at the selected value. It is also known that zirconia-based sensors may be similarly used. Other materials for use as exhaust gas sensor elements responsive to departures of a combustion mixture from a fuel rich value to a fuel lean value, and vice versa, by passing through the stoichiometric value are known.

The exhaust gases produced by fuel-rich combustion form an atmosphere which may be viewed as a reducing atmosphere. Many materials are known to respond electrically to changes in the chemistry of a reducing atmosphere. Exhaust gas sensors responsive to departure of a combustion mixture from the stoichiometric value to a fuel-rich or fuel-lean condition to produce a large scale change in an electrical characteristic are also known. Some of the reducing gas sensing materials also demonstrate this change which may ideally represent a step-function change. An example of this phenomenon is discussed in copending, commonly assigned U.S. Pat. No. 3,886,785, issued June 3, 1975 in the names of H. L. Stadler et al. The value of the stoichiometric responsive materials resides in this large scale excursion of an electrical parameter which may be utilized to directly and rapidly sense departure of the air/fuel ratio of the combustion mixture from stoichiometry.

It has become apparent that operation of an internal combustion engine with a combustion mixture at the stoichiometric value results in a combination of gas pollutants which combination is expensive and difficult to correct by means of exhaust gas reactors. For example, combinations of two or more such reactors are known to be required to effectively reduce the exhaust gas pollutants produced under such conditions to values which the Environmental Protection Agency of the United States Federal Government asserts to be an environmentally safe in internal combustion engine exhaust. While operation of the engine under either fuel-rich or fuel-lean conditions can overcome this difficulty, the presently available exhaust gas sensors function under fuel-rich conditions and the resulting excess consumption of fuel is most undesirable. Operation of the engine under fuel-lean conditions is therefore preferrable since the wasteful excess consumption can be avoided. The exhaust gases produced under such a situation constitute an oxidizing atmosphere and it is therefore a specific object of the present invention to provide a sensor capable of operation in an oxidizing environment to function as an air/fuel ratio sensor.

The operation of an internal combustion engine in the "lean regime," (that is, with an air/fuel ratio of from about 15 to about 22) and particularly at high values of the air/fuel ratio results in automatic lessening of the major exhaust gas pollutants ($CO$, $HC$ and $NO_x$). Removal of residual amounts of any of the major pollutants is therefore relatively simple. This relative simplicity of operation is predicated upon maintenance of the air/fuel ratio at a selected and precisely controlled value. Heretofore, reliable operation of the internal combustion engine within the lean regime at any one selected air/fuel ratio has been made virtually impossible due to the lack of a suitable sensor which could respond to variations in the air/fuel ratio from its selected value within the lean regime. It is therefore a specific object of the present invention to provide a sensor which is operative for combustion mixtures within the lean regime and which may be used to accurately and reliably monitor the air/fuel ratio of the combustion mixture provided to an internal combustion engine. It is a further object of the present invention to provide such a sensor, and an electrical system responsive to the sensor, to produce a control signal which may be used to maintain a desired, known exhaust gas chemistry. It is a still further object of the present invention to provide such a sensor which has an approximately linear change in the logarithm of resistance in response to changes in the exhaust gas chemistry, and in particular to changes in the partial pressure of oxygen within the exhaust gas. More particularly still, it is an object of the present invention to provide a sensor suitable for positioning within the exhaust system of an internal combustion engine and having a sensing element or member with an electrical characteristic which varies in a controllable and predictable fashion in the presence of changes in the exhaust gas chemistry produced by variations in the air/fuel ratio of a fuel-lean combustion mixture provided to the engine. It is also an object of the present invention to provide an electrical system, including the sensor of the present invention, for controlling an operational amplifier to produce an output signal which may be used to control or modulate the air/fuel ratio of a combustion mixture.

SUMMARY OF THE PRESENT INVENTION

The present invention provides an exhaust gas sensor having, as its active element, a cobalt monoxide ceramic member arranged so that its electrical resistance may vary in response to changes in the exhaust gas chemistry which variations may be measured electrically. The sensor is also provided with means for generating heat in the vicinity of the cobalt monoxide element to provide for rapidly heating this element to a temperature in excess of its minimum operating temperature. The cobalt monoxide active element of the present invention is provided in a substantially cylindrical form having a pair of electrodes applied to the axially opposite ends of the cylinder. A pair of electrical wires is coupled to the electrodes for application of a controlled electrical current from which a voltage signal indicative of variations in the resistance of the cobalt monoxide sensing element may be derived. The electroded ends of the cylindrical element are supported within a compatible ceramic housing material, such as alumina, which is provided with a transverse aperture to assure a flow of exhaust gases in close proximity to the surface of the sensing element. The heater wire is arranged in a helix wrapped about the housing structure and a cover member may be provided to protect the heater wire, the housing members, and the sensing element.

The present invention also provides an electrical circuit, including the cobalt monoxide ceramic sensing element of the present invention, for providing a pair of inputs to an operational amplifier such that the output signal of the operational amplifier may indicate by its magnitude the magnitude of any variation of the air/fuel ratio of the combustion mixture and, by its polarity, the quality of any variation in air/fuel ratio. Quality is intended to mean whether the excursion of the air/fuel ratio is an increase in fuel content or a decrease in fuel content from the fuel content at the selected air/fuel ratio.

DETAILED DESCRIPTION OF THE PREFERRED EMBODIMENT

Figure 1:
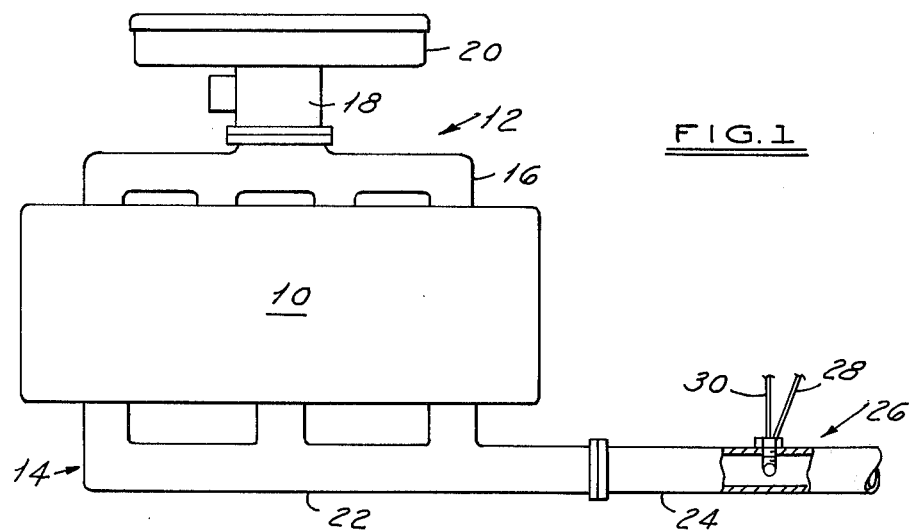
FIG. 1 is a schematic illustration of an internal combustion engine showing the installation of the present invention in the exhaust system thereof.

Referring now to the drawing wherein like numbers designate like structure throughout the various views thereof, FIG. 1 is an illustration showing an internal combustion engine 10 having an associated combustion mixture intake system 12 and an exhaust system 14. Intake system 12 is comprised of an intake manifold 16 fixedly coupled to the engine 10 and is arranged to provide a flow of the combustible air/fuel mixture to the intake ports, not shown, of the engine 10. An air/fuel mixture preparation device 18 is fixedly coupled to the intake manifold 16 upstream from the intake ports of the engine 10 and may be, for example, a carburetor or any other form of device for producing an air/fuel mixture. An intake air cleaner 20 is illustrated as being upstream from the mixture preparation device 18 and is of notoriously well known construction.

Air/fuel mixture preparation device 18 preferably includes an electrical means for modulating either the air or the fuel content of the air/fuel mixture in order to controllably vary the mixture ratio. The mixture ratio may be controllably varied electrically through the use of a continuous flow fuel delivery device having an electrically controllably metering orifice in conjunction with a carburetor or fuel injection system or through a scheduling control arranged to modulate the injector valve open time in an intermittent injection fuel injection system. Alternatively, the air content of the combustion mixture may be varied by an electrically controlled air valve within intake system 12. It will be appreciated that this brief description is intended to be merely illustrative and that a large variety of means and mechanisms is available to accomplish the desired result of modulating either the air or the fuel content of the air/fuel mixture in accordance with an electrical input signal derived as described hereinbelow with reference to FIGS. 2 and 3.

Exhaust system 14 includes an exhaust manifold 22 and an exhaust conduit 24. Exhaust conduit 24 may communicate with an exhaust gas reactor of the thermal or catalytic variety and may also communicate with an exhaust silencer such as a muffler in conducting the combustion by-product exhaust gases from the combustion chambers of the engine 10 to the atmosphere while reducing the gaseous and noise pollutants which are also by-products of the combustion process. An exhaust gas sensor 26 according to the present invention is threadedly received by a wall portion of conduit 24 so that the active portion of the exhaust gas sensor 26 extends into the interior region of conduit 24. First and second pairs of electrical leads 28, 30 extend from the exhaust gas sensor 26 and communicate with electrical apparatus as described herinbelow with reference to FIGS. 2 and 3. The precise placement of sensor 26 will depend upon temperature and other considerations such as accessibility, vibration and availability of electrical energy.

It will be appreciated that the various mechanical constituents of this system as hereinabove briefly described may be held in assembled relationship by any suitable means such as the well known and presently employed bolting of the various components together with the use of gaskets between adjacent components whereever necessary to avoid uncontrolled leakage at these joints. As thus described, internal combustion engine 10 with its air/fuel mixture intake system 12 and its exhaust system 14 may be a reciprocating piston internal combustion engine or may also be the more recently developed rotary internal combustion engine.

Figure 2:
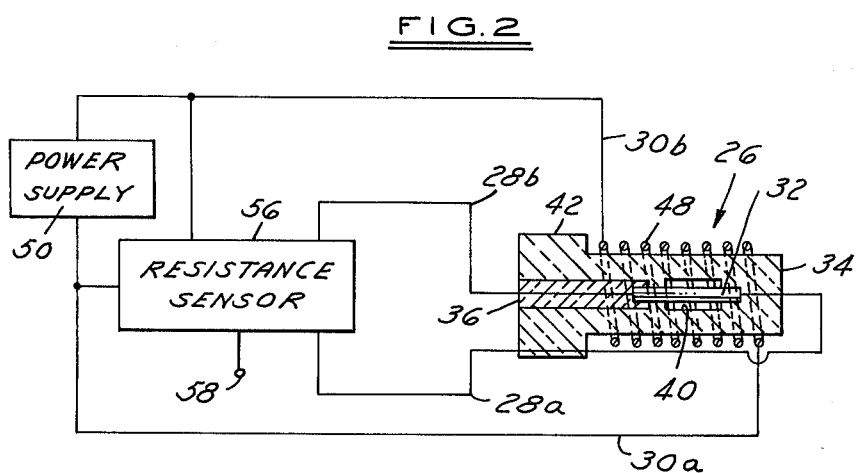
FIG. 2 is a diagrammatic view showing the sensor according to the present invention in section and including a block diagram of an electrical system associated with the sensor for deriving a useful output.
Figure 4:
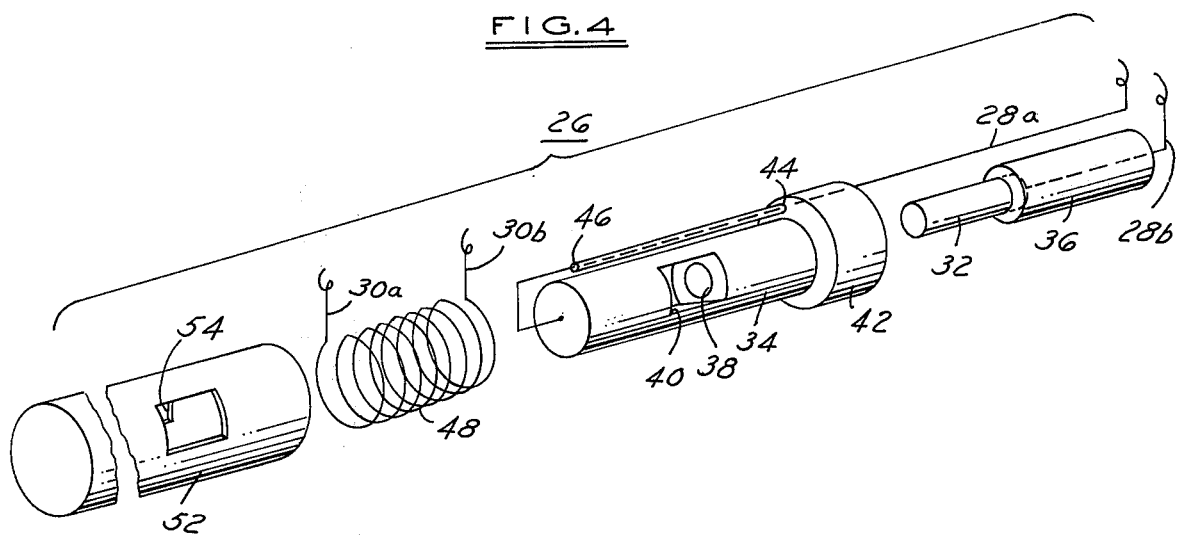
FIG. 4 is an exploded view of one embodiment of the sensor according to the present invention.

Referring now to FIGS. 2 and 4, the exhaust gas sensor 26 according to the present invention is illustrated in section view with an electrical block diagram (FIG. 2) and in an exploded view of the sensor per se (FIG. 4). The exhaust gas sensor 26 is comprised of a sensing element 32 supported at its ends by housing members 34, 36. As illustrated in FIGS. 2 and 4, sensing element 32 comprises a substantially cylindrical block or unit of cobalt monoxide ceramic material which is adapted on its axial ends for receipt of the pair of electrical leads 28a, 28b. For example, the axially remote ends of the generally cylindrical sensing element may be provided with an electrode forming coating of platinum paste material and the ends of wires 28a, 28b, which in this instance are preferably also platinum, are bonded to these surfaces. It will be appreciated that other sensing element geometrys and sensor configurations are contemplated. For example, the wafer geometry and configuration of the above-noted Stadler et al. U.S. Pat. No. 3,886,785 is considered to be feasible and to produce results comparable with those of the illustrated sensor 26.

In the illustrated embodiment, housing members 34, 36 are generally cylindrical members with housing member 36 sized to be received within a suitable axially extending bore provided within housing member 34. Housing member 36 is provided with a support recess arranged to receive one axial end of the sensing element 32. Housing member 34 is provided with an axially extending bore 38 which is sized to permit passage of, and receive, sensing element 32 upon insertion of sensing element 32 and housing member 36 within housing member 34. Housing member 34 is also provided with transverse bore 40 which is arranged to extend completely through housing member 34 and to be positioned to expose sensing element 32, intermediate the ends thereof, to the gaseous environment of the sensor 26. Transverse bore 40 is therefore operative to provide for communication of a flow of exhaust gases around, and in close proximity to, sensing element 32. Housing member 34 is also provided with a mounting flange 42 having a through passage 44. Hollow support member 46 is received within through passage 44. One lead, 28a, of the first pair of electrical leads 28 is arranged to extend through the hollow support member 46 for electrical communication with one end of sensing element 32 while the other electrical lead, 28b, of the first pair of electrical leads 28 communicates electrically with the other end of sensing element 32.

Heating coil 48 is arranged to surround housing member 34. Each end of heating coil 48 communicates with one lead of the second pair of electrical leads 30. This communication may be through flange portion 42 through cover member 52, or through hollow support member 46. The electrical leads 30 are arranged to communicate with an electrical power supply 50 for flow of a heating current through heating coil 48. aligned Cover member 52, as shown in FIG. 4, is arranged to encapsulate heater coil 48 and housing member 34. Cover member 52 therefore provides for protection of the heating coil 48 and of the sensing element 32 to permit ease of handling of the sensor 26 during its installation in the exhaust system 14. Cover member 52 also proves for isolation of heater coil 48 from the cooling effects of the major flow of the exhaust gas stream. Cover member 52 is provided with a pair of transversely aligned windows 54 which are positioned to be in registry with the transverse bore 40 when cover member 52 engages mounting flange portion 42. Thus, cover member 52 will not hinder or impede the flow of gases around the sensing element 32.

With particular reference now to FIG. 2, sensor 26 is shown in a sectional view with cover member 52 removed. An electrical system operative with the sensor 26 of the present invention is also illustrated in a block diagram. The first pair of electrical leads 28 and the power supply 50 communicate with resistance responsive controller means 56. Upon the application of electric power to heating coil 48, heating coil 48 will operate to elevate the temperature of the sensing element 32 to assist in rapid heating of sensing element 32 to its minimum operating temperature of approximately 900°C.

At temperatures below about 900°C and at partial pressures of oxygen in the exhaust system 12 characteristic of operation of an internal combustion engine in the lean regime, cobalt monoxide undergoes a phase change to a form of oxide which does not exhibit the desired resistance variations. Heating coil 48 enables rapid heating sufficient to encourage the phase change to the monoxide phase of any surface material which may have converted during the previous cool-down. However, the exhaust system 14 of an internal combustion engine cools sufficiently rapidly that the total mass of material converting to the desired oxide phase will be slight.

We have determined that the logarithm of the electrical resistance of cobalt monoxide ceramic material varies in a generally linear fashion in response to changes in the partial pressure of oxygen in the exhaust gas by-products of lean regime combustion when the temperature of the sensing element is maintained above about 900°C. Furthermore, this resistance change is repeatable, predictable and occurs with a response time of less than about 1 second. The region of partial pressures of oxygen over which this resistance change occurs corresponds to the partial pressures of oxygen predicted by chemical computation to occur as the exhaust gas by-products of combustion of a mixture having an air/fuel ratio in the lean regime.

We have determined that the electrical resistance of cobalt monoxide ceramic is related to the partial pressure of oxygen by the expression $$R \propto P_{O_2}^{-1/4} e^{+E/(KT)}$$

where $R$ is the resistance in ohms, $P_{O_2}$ is the partial pressure of oxygen in Atmospheres, $e$ is the base of the natural logarithm, $E$ is the activation energy of the material in electron volts, $T$ is the temperature in degrees Kelvin and $K$ is the Boltzmann constant in electron volts per degree. As the partial pressure of oxygen drops below about $10^{-6}$ Atmosphere the power in the above expression changes gradually from $-1/4$ to $-1/6$. For cobalt monoxide ceramic material, E is approximately equal to one-half (0.5) of an electron volt and the dependence of the expression upon temperature can be seen to be slight. Thus, accurate temperature control above about 900°C is not required. By providing a known voltage potential between leads 28a, 28b of the first pair of electrical leads 28 and by measuring the amount of current flowing therethrough, the partial pressure of oxygen of the gaseous environment of sensing element 32 can be determined.

In order to maintain operation of internal combustion engine 10 at a selected air/fuel ratio within the lean regime, i.e., where uncombusted and therefore excess oxygen may exist within the exhaust gases produced as by-products of the combustion process, the partial pressure of oxygen of the exhaust gas stream must be maintained substantially constant at a selected value. By electrically monitoring resistance changes of the sensing element 32 variations in this partial pressure of oxygen may be detected. By suitably operating upon detected changes in the resistance measurements, resistance responsive controller means 56 may be arranged to provide an electrical signal, at output terminal 58, which may be made representative of the amount of change necessary in either the air, or the fuel, content of the air/fuel mixture provided by mixture preparation device 18 to maintain a selected partial pressure of oxygen within the exhaust system 14.

Figure 3:
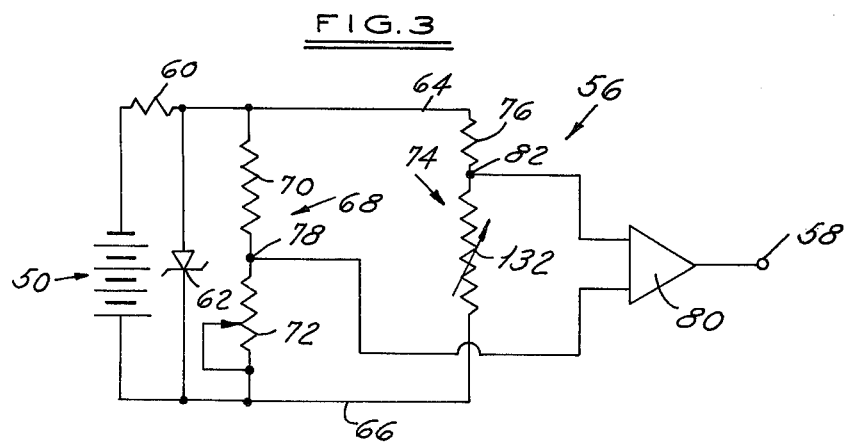
FIG. 3 is an electrical circuit illustrating one embodiment of the block diagram system shown in FIG. 2.

Referring now to FIG. 3, an electrical schematic of the resistance responsive controller means 56 of FIG. 2 is shown. The circuit of this figure also includes a representation of power supply 50 in the form of a battery and incorporates the variable electrical resistance of sensing element 32 as variable resistance 132. The circuit of FIG. 3 includes limit resistor 60 and zener diode 62 which are cooperative to provide a regulated voltage across the conductors 64, 66. Reference voltage divider 68 is comprised of a fixed resistance 70 and a variable resistance 72, such as a potentiometer, connected electrically in series between conductors 64, 66. Sensor voltage divider 74 is similarly comprised of a fixed resistance 76 connected electrically in series with the variable resistance 132 formed by sensing element 32. The reference voltage junction 78, formed by the junction of fixed resistance 70 with variable resistance 72, is communicated to one input terminal of operational amplifier 80. Sensor voltage junction 82, formed by the junction of fixed resistance 76 with variable resistance 132, is communicated to the other input terminal of operational amplifier 80. Operational amplifier 80 may be, for example, a type $\mu$ 741 operational amplifier. This type of operational amplifier is available through a large number of sources under the identifying number $\mu$ 741.

The variable resistance 72 in the reference voltage divider portion of the network of FIG. 3 may be calibrated to provide a voltage at reference junction 78 which is exactly equal to the voltage appearing at sensor voltage junction 82 when the partial pressure of oxygen in the atmosphere in which sensor 26 is immersed is exactly equal to that corresponding to operation of the internal combustion engine with the combustion mixture at the desired air/fuel ratio. By arranging operational amplifier 80 to produce at its output terminal 58 a voltage signal which is a selected multiple of the difference between the voltage values appearing on its input terminals, operation of the internal combustion engine 10 at the precisely desired air/fuel ratio will result in a zero voltage signal appearing on the output terminal 58. Any excursion in the air/fuel ratio of the combustion mixture away from the desired value will result in a shift in the voltage value appearing at sensor voltage junction 82 which, when compared with the voltage appearing at reference voltage junction 78, will result in an output signal appearing at terminal 58. Thus, the signal appearing at output terminal 58, including a zero signal, will indicate the electrical resistive value of sensing element 32 relative to a preselected value and hence the partial pressure of oxygen in the environment of the sensor 26. The magnitude of the signal appearing at terminal 58 will therefore be indicative of the magnitude of the variation of the air/fuel ratio from the desired value while the polarity of the signal appearing at output terminal 58 will be indicative of the nature or quality of the excursion. For example, a positive polarity signal appearing at junction 58 may indicate that the air content of the air/fuel mixture is excessive resulting in an increase in the air/fuel ratio while a negative polarity signal appearing at output terminal 58 may indicate that the air content of the air fuel mixture is inadequate producing a decrease in the air/fuel ratio of the combustion mixture. The magnitude and the polarity of the output signal generated by operational amplifier 80 may be readily tailored to be directly compatible with the particular modulation device selected for inclusion in intake system 12 such that the polarity and the magnitude of signal appearing at output terminal 58 will automatically command the proper corrective measures to maintain the air/fuel ratio of the combustion mixture at the selected value. It will be appreciated that the specific electrical network illustrated in FIG. 3 is representative only and that other electrical networks may also be utilized with the present invention to achieve beneficial results. For example, a network comparable to that illustrated in FIG. 3 of the above-noted Kushide et al U.S. Pat. No. 3,868,846 may be utilized.

Figure 5:
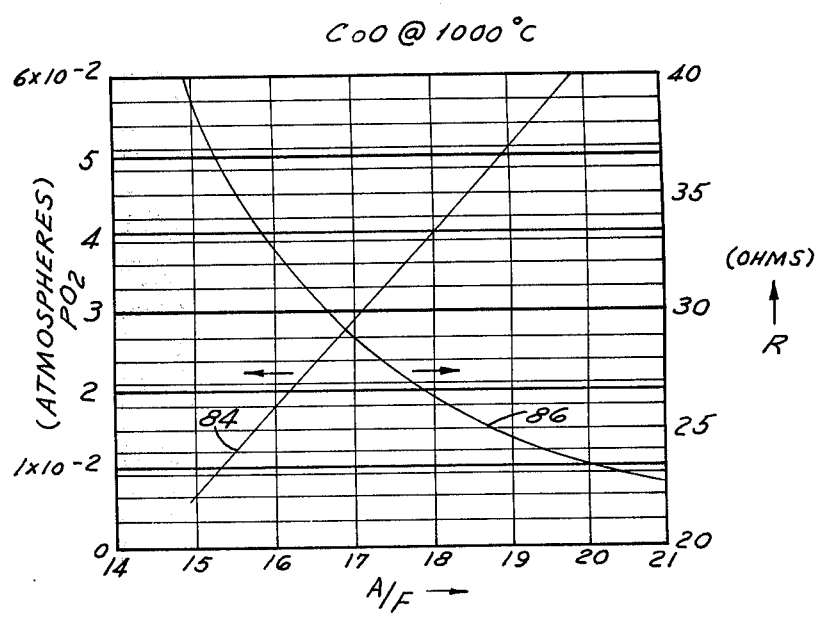
FIG. 5 is a graph illustrating the electrical behavior of the present invention in terms of engine operation.

Referring now to FIG. 5, a graph is shown illustrating, by curve 84, the relationship of the partial pressure of oxygen present in volume percent in the exhaust gases produced by combustion of various air/fuel ratio combustion mixtures. FIG. 5 also includes a graph illustrating, by curve 86, typical resistance value for sensing element 32 at the various illustrated air-to-fuel ratios. It will be appreciated that the ohmic values given for various resistances are illustrative only and that specific resistance values will depend upon the particular geometry and dimensions employed for sensing element 32. However, the illustrated differential resistance, in percent, is typical. For example, the resistance of the cobalt monoxide ceramic sensing element 32 is larger, by approximately 70 percent, at an air/fuel ratio of 15 than it is at an air/fuel ratio of 20. Curve 86 is linear if graphed on a logarithmic scale.

Thus it can be seen that the present invention readily accomplishes its stated objectives. By utilizing a cobalt monoxide ceramic sensing element, fabricated from commercially available forms of pure cobalt monoxide according to any of the well known ceramic formation techniques, a sensor which demonstrates a repeatable and uniquely defined resistance value for differing partial pressures of oxygen results. By supporting the ends of a cylinder of cobalt monoxide ceramic sensor material with a compatible ceramic material such as alumina the properties of the cobalt monoxide ceramic do not demonstrate any long term changes which would effect the electrical characteristics of the cobalt monoxide ceramic material and the sensing element is well supported against vibration. By utilizing a surrounding heating coil 48, the cobalt monoxide ceramic material may be brought rapidly to its operating temperature so that the sensor 26 may become functional in a shorter amount of time from an internal combustion engine startup and may be maintained above 900°C during operation so that the monoxide phase of the cobalt oxide ceramic may be maintained. Use of the cover member 52 facilitates handling and provides for protection of the device when being handled while providing insulation against thermal shock and any cooling of the sensing element 32 or the heating coil 48 caused by the absorption of heat by the flow of the exhaust gas stream.

We claim:

1. A sensor for sensing the partial pressure of oxygen gas within a gas conduit system for exhausting the gaseous combustion by-products of fuel-lean combustion from a combustion chamber of an engine, comprising in combination:

a cobalt monoxide ceramic sensing element having an electrical resistive path;

electrically conductive means attached to said sensing element at opposite ends of said electrical path, operative to provide a flow of electric current through said sensing element generally along said electrical path;

housing means for receiving and supporting said sensing element, said housing means including means for attachment to a wall portion of the gas conduit system and being arranged to expose a substantial portion of the surface of said sensing element to the gaseous combustion by-products within the gas conduit system; and electrical means communicating with said conductive means for generating an electrical signal having a magnitude and polarity indicative of the electrical resistance value of said sensing element along said electrical path whereby the partial pressure of oxygen within the gaseous combustion by-products and hence the air/fuel ratio of the combustion mixture may be defined.

2. The sensor of claim 1 wherein said electrical means comprise:

reference means for generating a reference voltage value indicative of a desired air/fuel ratio for the combustion mixture; and comparison means for comparing said reference value with the value indicative of the electrical resistance of the sensing element, said comparison means operative to generate said electrical signal whereby said generated electrical signal is also indicative of the magnitude and quality of the excursion of the air/fuel ratio from the desired air/fuel ratio.

3. The sensor of claim 1 including cover means attached to said housing means and arranged to surround and protect said housing means and said sensing element.

4. The sensor of claim 3 wherein said cover means include means defining at least two apertures arranged to provide a flow of the gaseous combustion by-products over the surface of at least a portion of said sensing element.

5. The sensor of claim 1 including heating means, auxiliary to the combustion by-products, for heating said sensing element to a temperature above about 900°C.

6. In a system for monitoring the air/fuel ratio of the combustion mixture provided to an internal combustion engine intended to operate under steady state conditions at a preselected air/fuel ratio wherein an exhaust gas sensor is situated within the stream of exhaust gases produced by the engine and is arranged to produce an electrical signal indicative of the partial pressure of oxygen in the exhaust gases and including electrical means communicating with and responsive to the sensor and arranged to generate an electrical signal indicative of the air/fuel ratio of the combustion mixture, the improvement wherein the exhaust gas sensor is comprised of a cobalt monoxide ceramic sensing element connected electrically in series with a source of electrical energy and the electrical means are arranged to respond to the current flow through said cobalt monoxide sensing element to generate an output signal having a magnitude and polarity indicative of excursion of the air/fuel ratio of the combustion mixture from a selected value in the lean regime.

7. The system of claim 6 wherein said electrical means comprise:

reference means for generating a reference voltage value indicative of a desired air/fuel ratio for the combustion mixture; and comparison means for comparing said reference value with a value indicative of the electrical resistance of the sensing element, said comparison means operative to generate said electrical signal, whereby said generated electrical signal is also indicative of the magnitude and quality of the excursion of the air/fuel ratio from the desired air/fuel ratio.

8. The system of claim 6 including cover means attached to said housing means and arranged to surround and protect said housing means and said sensing element.

9. The system of claim 8 wherein said cover means include means defining at least two apertures arranged to provide a flow of the gaseous combustion by-products over the surface of at least a portion of said sensing element.

10. The system of claim 6 including heating means, auxiliary to the exhaust gases, for maintaining the temperature of the cobalt monoxide above about 900°C in operation.

* * * * *